United States Patent
Perriard et al.

(10) Patent No.: US 10,945,911 B2
(45) Date of Patent: Mar. 16, 2021

(54) SYSTEM FOR ADJUSTING PRESSURE LOCALLY ON THE SKIN AND SUBCUTANEOUS TISSUE

(71) Applicant: ECOLE POLYTECHNIQUE FEDERALE DE LAUSANNE (EPFL), Lausanne (CH)

(72) Inventors: Yves Perriard, Neuchâtel (CH); Zoltan Pataky, Gland (CH); Daniel Grivon, Neuchâtel (CH); Yoan René Cyrille Civet, Marin (FR)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 494 days.

(21) Appl. No.: 15/524,676

(22) PCT Filed: Nov. 6, 2015

(86) PCT No.: PCT/IB2015/058574
§ 371 (c)(1),
(2) Date: Aug. 16, 2017

(87) PCT Pub. No.: WO2016/075599
PCT Pub. Date: May 19, 2016

(65) Prior Publication Data
US 2017/0348181 A1 Dec. 7, 2017

(30) Foreign Application Priority Data
Nov. 10, 2014 (FR) ...................................... 1460869

(51) Int. Cl.
*A61H 9/00* (2006.01)
*A43B 13/20* (2006.01)
(Continued)

(52) U.S. Cl.
CPC ......... *A61H 9/0078* (2013.01); *A43B 13/203* (2013.01); *A61B 5/1036* (2013.01);
(Continued)

(58) Field of Classification Search
CPC .. A61H 9/005; A61H 9/0078; A61H 23/0218; A61H 2023/0227;
(Continued)

(56) References Cited

U.S. PATENT DOCUMENTS 5,379,471 A * 1/1995 Holdredge ........... A61G 5/1043
297/DIG. 8
5,813,142 A 9/1998 Demon
(Continued)

FOREIGN PATENT DOCUMENTS

CA 2056176 C 6/1992

OTHER PUBLICATIONS

French Search Report dated Jul. 21, 2015.
(Continued)

*Primary Examiner* — Tu A Vo
*Assistant Examiner* — Alexander Morales
(74) *Attorney, Agent, or Firm* — Andre Roland S.A.; Nikolaus Schibli

(57) ABSTRACT

A system for adjusting pressure locally acting on the skin including a set of adjacent modules distributed so as to form a layer each module includes a cushion capable of changing shape and comprising a cavity, a valve, a tank, and a pressure sensor, wherein the cavity and the tank are in communication with each other by means of the valve, and the sensor is placed so as to sense pressure directly or indirectly acting on the cushion and a feedback loop arranged such as to increase or decrease the change in the shape of the cushion on the basis of the pressure detected by the sensor.

12 Claims, 9 Drawing Sheets

(51) Int. Cl.
*A61B 5/103* (2006.01)
*A61H 23/02* (2006.01)

(52) U.S. Cl.
CPC ......... *A61H 9/005* (2013.01); *A61H 23/0218* (2013.01); *A61H 2023/0227* (2013.01); *A61H 2201/0134* (2013.01); *A61H 2201/0192* (2013.01); *A61H 2201/1207* (2013.01); *A61H 2201/1238* (2013.01); *A61H 2201/1246* (2013.01); *A61H 2201/1409* (2013.01); *A61H 2201/164* (2013.01); *A61H 2201/1654* (2013.01); *A61H 2201/1664* (2013.01); *A61H 2201/5002* (2013.01); *A61H 2201/5005* (2013.01); *A61H 2201/5007* (2013.01); *A61H 2201/5056* (2013.01); *A61H 2201/5071* (2013.01); *A61H 2205/12* (2013.01); *A61H 2205/125* (2013.01)

(58) Field of Classification Search
CPC .... A61H 2201/0134; A61H 2201/0192; A61H 2201/1207; A61H 2201/1238; A61H 2201/1246; A61H 2201/1409; A61H 2201/164; A61H 2201/1654; A61H 2201/1664; A61H 2201/5002; A61H 2201/5005; A61H 2201/5007; A61H 2201/5056; A61H 2201/5071; A61H 2205/12; A61H 2205/125; A43B 13/203; A61B 5/1036
See application file for complete search history.

(56) References Cited

U.S. PATENT DOCUMENTS

| | | | |
|---|---|---|---|
| 7,219,449 B1* | 5/2007 | Hoffberg | A43B 1/0054 36/29 |
| 7,409,735 B2 | 8/2008 | Kramer | |
| 8,024,828 B2* | 9/2011 | Nihei | A61G 7/05776 5/654 |
| 2003/0120353 A1 | 6/2003 | Christensen | |
| 2006/0075569 A1* | 4/2006 | Giori | A47C 27/088 5/709 |
| 2006/0085919 A1* | 4/2006 | Kramer | A47C 27/083 5/713 |
| 2006/0112489 A1* | 6/2006 | Bobey | A61B 5/1115 5/655.3 |
| 2006/0123548 A1* | 6/2006 | Heath | A47G 9/10 5/644 |
| 2006/0248750 A1 | 11/2006 | Rosenberg | |
| 2009/0144906 A1* | 6/2009 | Satoh | A61G 7/05776 5/655.3 |
| 2013/0326912 A1* | 12/2013 | Lindsay | A43B 3/00 36/103 |
| 2014/0165427 A1* | 6/2014 | Molyneux | A47C 27/088 5/709 |

OTHER PUBLICATIONS

French Written Opinion dated Jul. 21, 2015.
International Search Report dated Mar. 2, 2016.
Written Opinion of the International Search Authority dated Mar. 2, 2016.

* cited by examiner

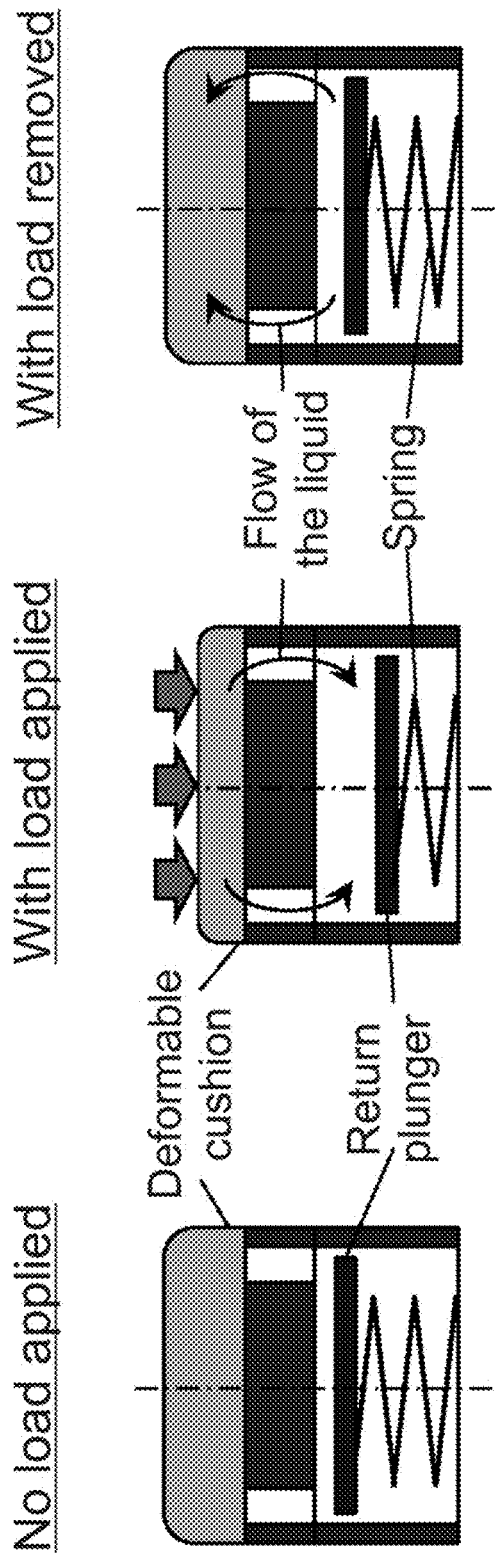

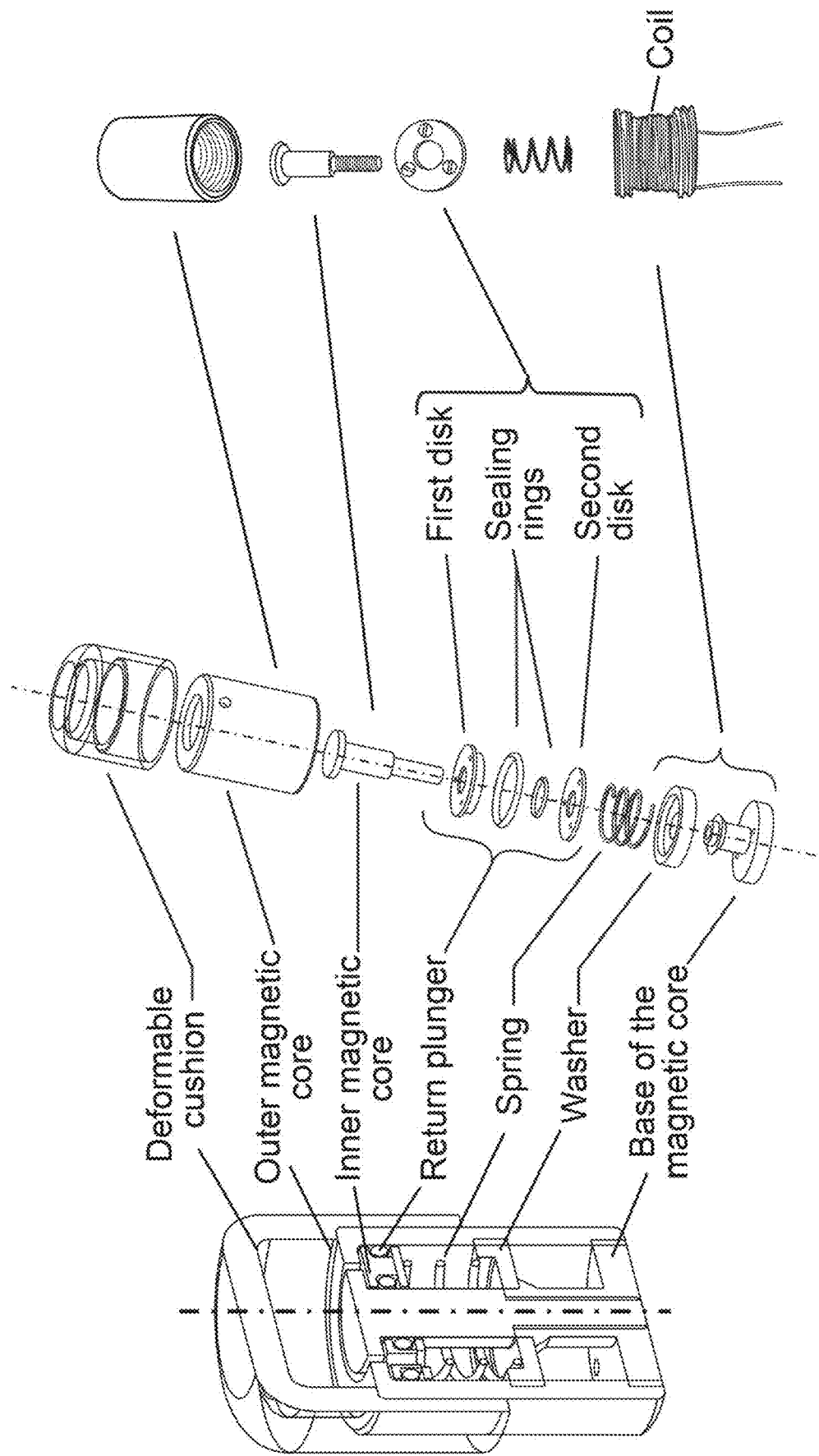

SYSTEM FOR ADJUSTING PRESSURE LOCALLY ON THE SKIN AND SUBCUTANEOUS TISSUE

CROSS REFERENCE TO RELATED APPLICATIONS

The present application is a U.S. national stage application of PCT/IB2015/058574 filed on Nov. 6, 2015 designating the United States, and claims foreign priority to French patent application FR 1460869 filed on Nov. 10, 2014, the contents of both documents being herewith incorporated by reference in their entirety.

FIELD OF THE INVENTION

The invention relates to adjusting the pressure that may be exerted locally on the skin and subcutaneous tissue, for example on the sole of the foot. It can be used advantageously in the medical sector or in sport.

PRIOR ART

People suffering from diabetes mellitus and diabetic neuropathy may develop wounds and ulcers on the sole of the foot. One of the causes behind the formation of these plantar ulcers is connected to the presence of areas of excessive plantar pressure, which may be localized across the entire sole of the foot, in most cases in the region of the heads of the metatarsals.

At present, the treatment of plantar ulcers in diabetic patients is limited mainly to passive systems, which simply ease the load on the region of the foot at risk (either with a tailor-made plaster or plaster cast, off-loading shoe or sole, or with a system allowing the creation of holes in a specific sole). With these systems, the rate of recurrence of foot ulcers is very high since, after these therapeutic devices have been removed (after recovery), the local plantar pressure increases again or the patient develops one or more new areas of excessive plantar pressure in another region of the feet. The therapeutic devices currently in use do not allow the plantar pressure to be redistributed in a balanced and uniform manner that is adapted to the everyday activities of patients.

There are several systems, disclosed in particular in the patent applications US2003/120353 A1 and US2006/0248750 A1, which detect the pressure at various locations of the sole of the foot or which automatically redistribute the plantar pressure.

The application US2003/120353 A1 describes an independent module having variable stiffness that is controllable in response to a variable load. This module is composed of two vertically arranged chambers which contain a liquid of variable viscosity (magneto-rheological or electro-rheological) and which are placed in communication with each other via an orifice. The change of viscosity brought about in the area of the orifice makes it possible to regulate the flow of the liquid from one chamber to the other, which is directly linked to the deformation of the module and therefore to a different response according to the load that is applied.

In the abovementioned system, only one or two modules (of relatively large size) are used, which serve as shock absorbers.

In addition, this system does not take into account the problems associated with mechanical guiding/controlling of the vertical deformation of the modules. Indeed, no structure is described for avoiding twisting of the module and for keeping the diameter of the orifice constant. The lack of support for the mechanical guiding can cause blockage of the module (on account of the high shearing forces that arise when the foot makes contact with the ground) and uncontrolled deformation of the orifice.

The application US2006/0245750 A1 describes a shoe with a sole that is divided into flexible chambers (cushions) which are filled in particular with rheological fluid having the ability to change viscosity if subjected to a magnetic/electric field.

The various chambers are interconnected by "communication channels" which allow the fluid to pass from one cushion to the adjacent cushion. Each channel has a magneto-rheological (electro-rheological) valve capable of changing the viscosity of the fluid inside the channel and of thereby increasing the resistance with which the liquid can flow.

Arranging the valves alongside the cushions has a number of disadvantages, in particular:

- Difficulty in integrating the rigid parts of the valves (necessarily present in order to be able to obtain sufficient efficacy of the system) with the rest of the sole which is in contact with the foot and is normally flexible.
- Considerably reduced density of the cushions.
- Increased complexity of the system (e.g. 9 communicating modules require 12 control valves; cf. FIG. 1).
- Reduced efficacy and flexibility of the system on account of the difficulty in exchanging liquid between the modules that are not adjacent.

There is therefore a need to reduce, if not eliminate, all of these disadvantages.

BRIEF DESCRIPTION OF THE SEVERAL VIEWS OF THE DRAWINGS

FIGS. 6A to 6C show exemplary views of different states of the variable stiffness module;

FIGS. 7A to 7C show different views of the components that can form the variable stiffness module with a mechanical spring;

DESCRIPTION OF THE INVENTION

The disadvantages of the prior art are greatly reduced, if not totally eliminated, by virtue of the present invention which relates to a system for adjusting the pressure acting locally on the skin and subcutaneous tissue. The system comprises a set of adjacent modules distributed in such a way as to form a layer; each module comprises the following elements arranged along a same direction: a deformable cushion comprising a cavity, a valve, a reservoir, and a pressure sensor.

The cavity and the reservoir communicate by way of the valve, and the sensor is arranged in such a way as to detect a pressure acting directly or indirectly on the cushion. To this end, it can be arranged on the wall of the cushion (direct measurement) or inside the cavity. In the latter case, the pressure of the liquid is measured (indirect measurement). The system additionally comprises a feedback loop arranged in such a way as to increase or reduce the deformation of the cushion according to the pressure detected by the sensor.

Advantageously, the system according to the invention comprises several miniaturized and adjacent modules which cover the surface of the forefoot and/or of the heel. They are arranged with a sufficient density to correctly detect the different zones of excessive pressure. The system is preferably capable of modifying the stiffness of each of the modules (thus permitting their deformation) and of thereby permitting a redistribution.

The system according to the invention can also include guide means which mechanically constrain the displacement of an element arranged in the reservoir (plunger or elastic membrane). In addition, any shearing force that may come into play in the contact between foot and module is taken up by the cushion without adversely affecting the functioning of the actual module.

Figure 1:
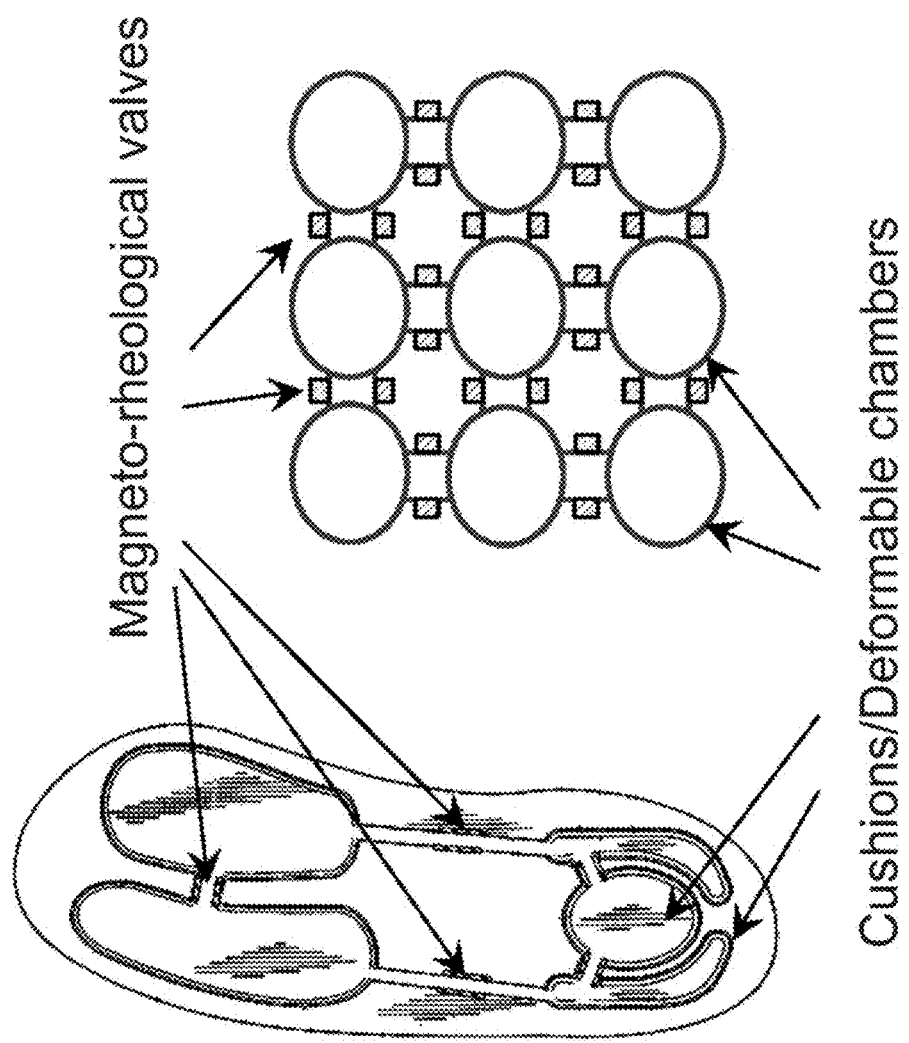
FIG. 1 depicts a system according to the prior art.
Figures 2A, 2B:
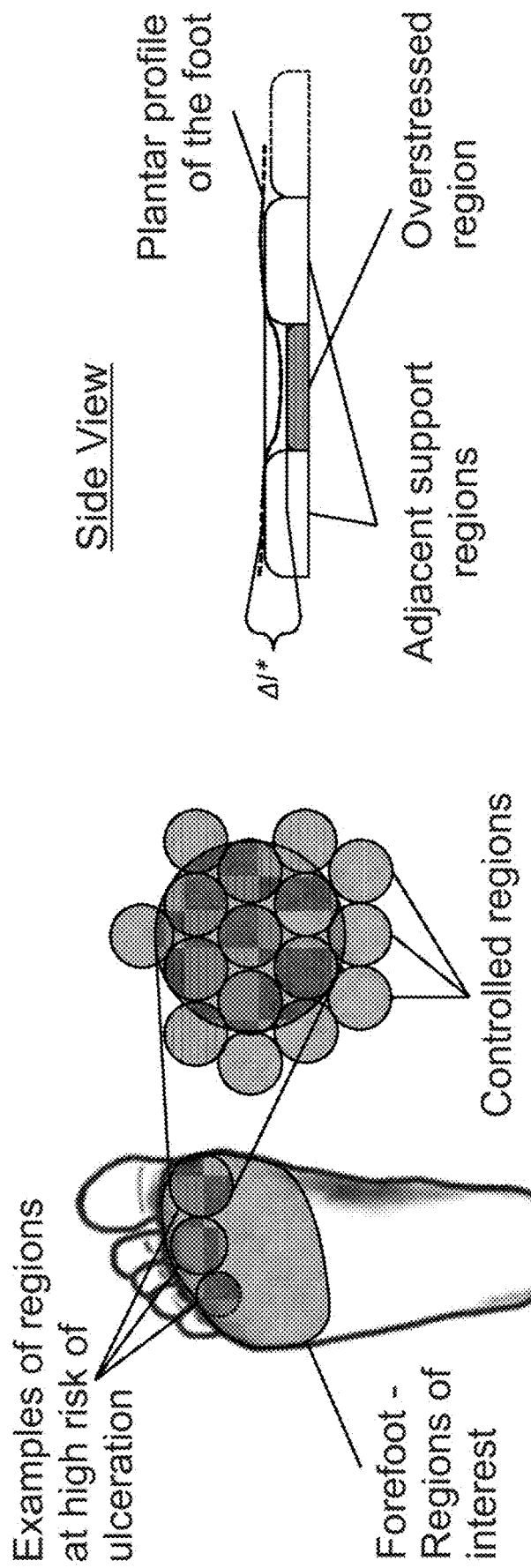
FIGS. 2A and 2B show different views of the system that can change the stiffness/pliability in different zones below the surface.

The modules can be "fluidically" independent or can communicate with each other. Each module defines a certain surface area. The set of modules makes it possible to change the stiffness/pliability in different zones below the surface of the system, for example a foot (FIGS. 2A and 2B). The system according to the invention in particular solves the problems of localized excessive pressure on the plantar surface of the feet. The system is capable of measuring and detecting the zones that have pressure peaks and of adapting its shape in order to redistribute the latter homogeneously. It is thus possible to control the height of each of the modules in order to modify the shape of the sole, dynamically when the patient moves. The change in the properties of each module of the sole (and therefore of the sole itself) is effected in relation to the information obtained by the pressure measurements of each of the sensors present on the different modules.

Figure 3:
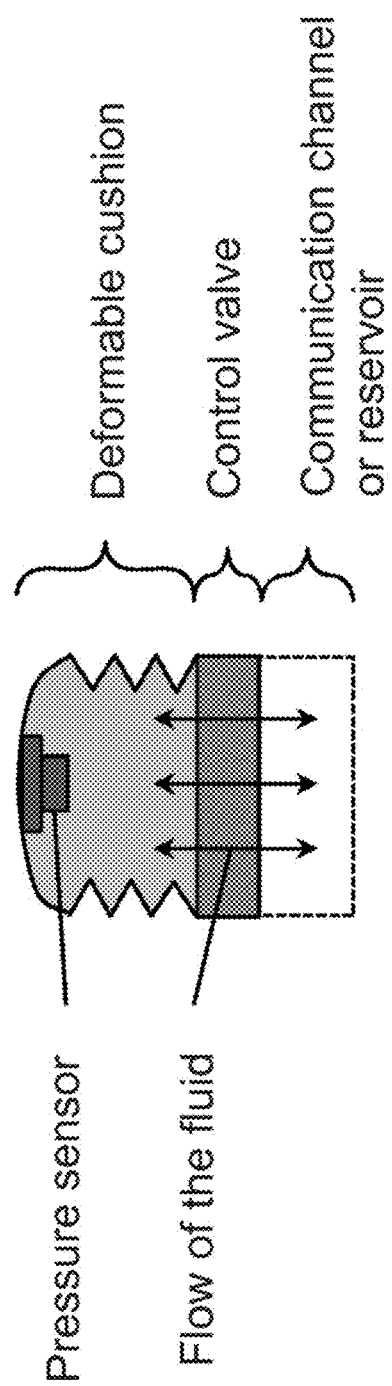
FIG. 3 shows an exemplary view of the individual module with a cushion, a reservoir, and a control valve.

A module is composed of three main parts (FIG. 3), namely (i) a deformable cushion having a cavity intended to receive a fluid, (ii) a reservoir, and (iii) a control valve arranged between the cushion and the reservoir.

According to one embodiment of the invention, the cushion is arranged in the upper part of the module. It is made of a flexible and deformable material. The geometry of the cushion can be of a bellows shape. Other geometries facilitating the deformation in a preferential direction (here vertical) are also possible. The cushion is filled with an incompressible fluid (water, oil, magneto-rheological fluid, etc.). In the variant in FIG. 3, a pressure sensor is arranged in the upper part and on the inner face of the wall of the cushion. This measurement permits determination of the contact pressure between the patient's foot and the deformable cushion. Other pressure sensors can also be used inside or outside the cushion. Any other arrangement of the measurement system permitting determination of the contact pressure between the foot and the actual module may be envisioned as a possible solution.

The valve controls the flow rate of the fluid moving between the cavity of the cushion and the reservoir. Preferably, the valve is designed to occupy the same surface area as that of the cushion. This vertical arrangement of the main parts of the module makes it possible to maximize the density of modules for a given surface area. More precisely, any sort of valve having the ability to satisfy the demands of dimension, miniaturization, energy consumption, maximum attainable pressure and maximum flow rate for the application and configuration (below the deformable cushion) may be considered as possible solutions.

The fluid entering the reservoir comes from the cavity of the cushion and, if the modules are fluidically connected, of the other modules.

The functioning of a module can be defined by three states:

Valve closed: The cushion maintains its initial position and remains rigid, the fluid being incompressible and having no possibility of entering and/or leaving the cavity. In this case, if an external pressure (e.g. the patient's foot) is exerted on the module, the cushion does not deform. The module thus acts as a rigid sole element.

Valve open: The cushion is able to deform since the fluid contained in the cavity can move into the reservoir.

Control of the flow rate of the fluid: Acting in the area of the valve. In this case, the module will have a variable stiffness.

For a normal liquid, the flow rate is controlled by increasing or reducing the opening of the valve.

Alternatively, a magneto-rheological fluid (MRF) and an MRF valve may be used.

An MRF is composed of a non-magnetic liquid (water or oil) in which magnetic particles (generally iron powder) are dispersed. The main property of this liquid is its ability to change viscosity when subjected to a magnetic field.

An MRF valve is composed of a magnetic circuit and of an element creating a magnetic field (for example a coil, magnet, etc.). The interaction of the magnetic field and of the MRF produces a change of viscosity of the latter and therefore modifies its passage through the valve. If the strength of the magnetic field is sufficiently high, the MRF becomes viscous, to the point that its flow rate through the valve is close to or equal to zero.

As has been indicated above, the modules can be arranged and connected in different ways.

I. Communicating Modules

Figure 4:
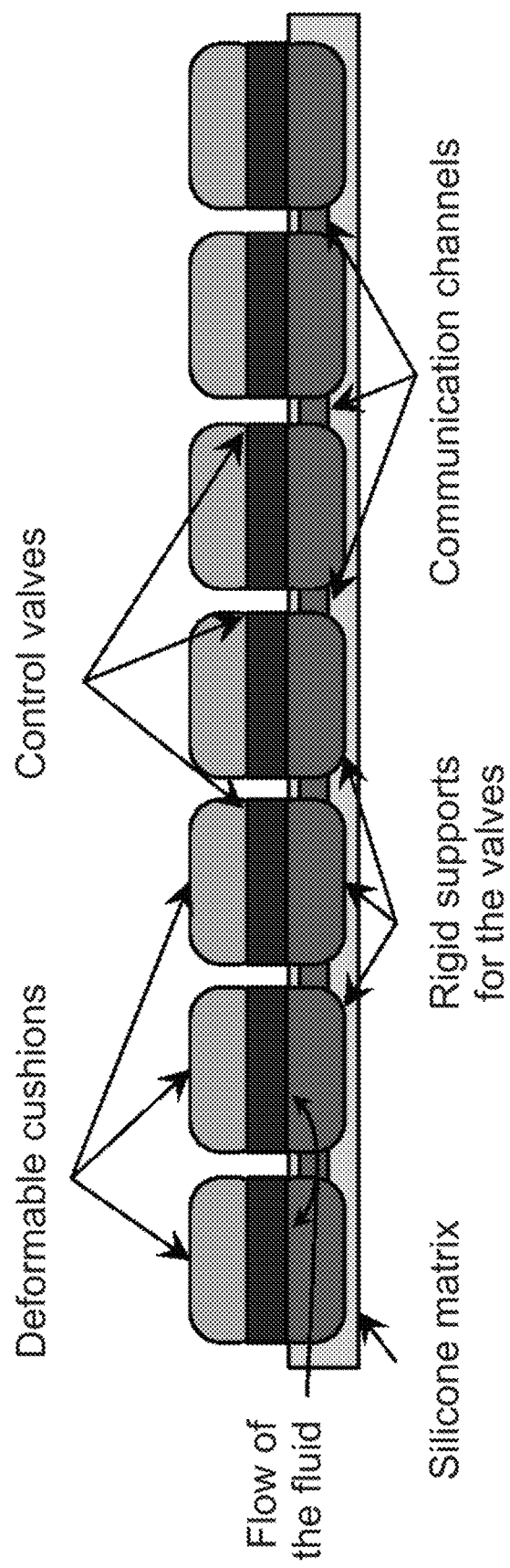
FIG. 4 shows a side view of the system with a plurality of variable stiffness modules.
Figure 5:
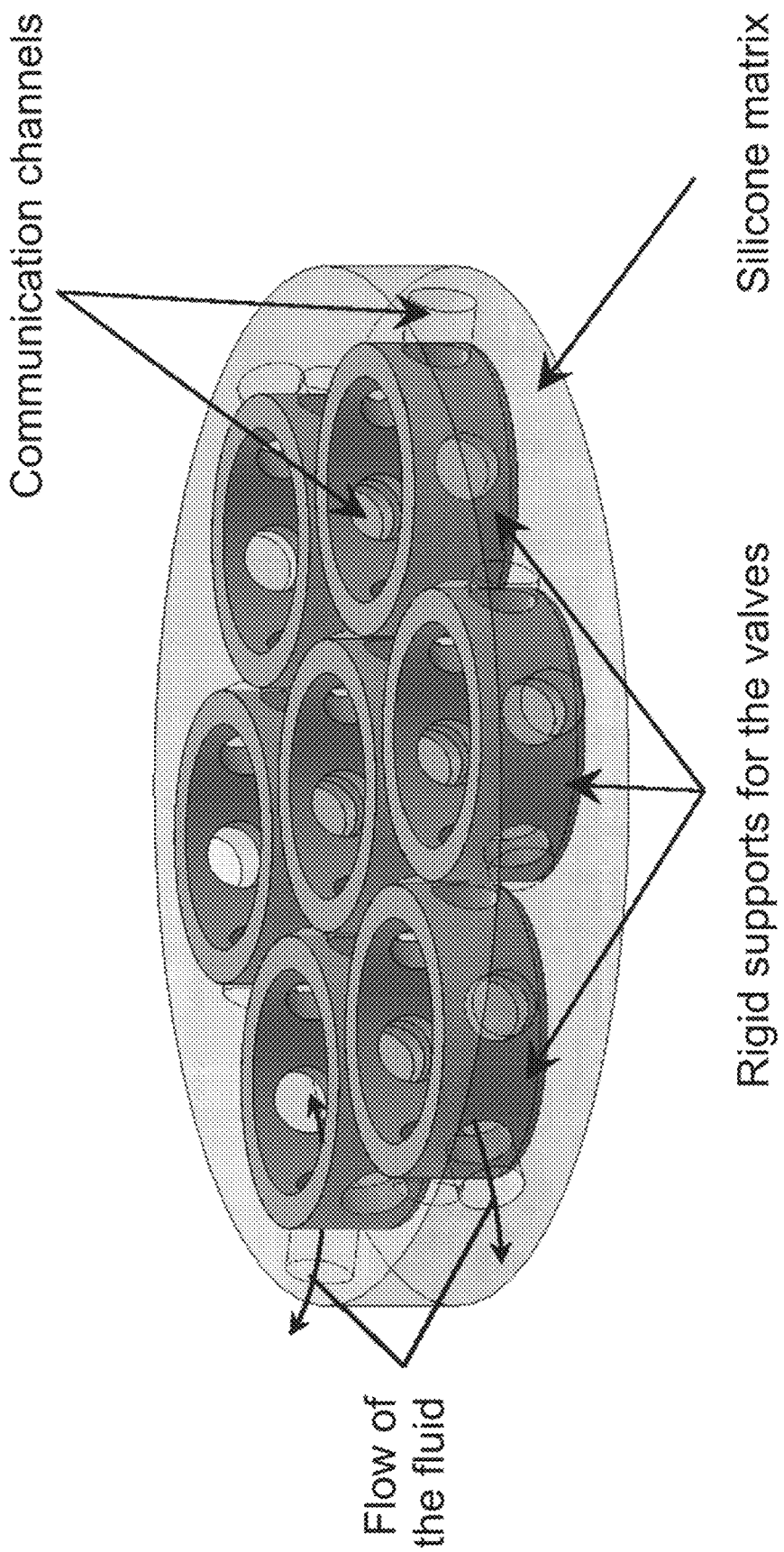
FIG. 5 shows a perspective view of the system with a plurality of variable stiffness modules.
Figures 8A, 8B, 8C:
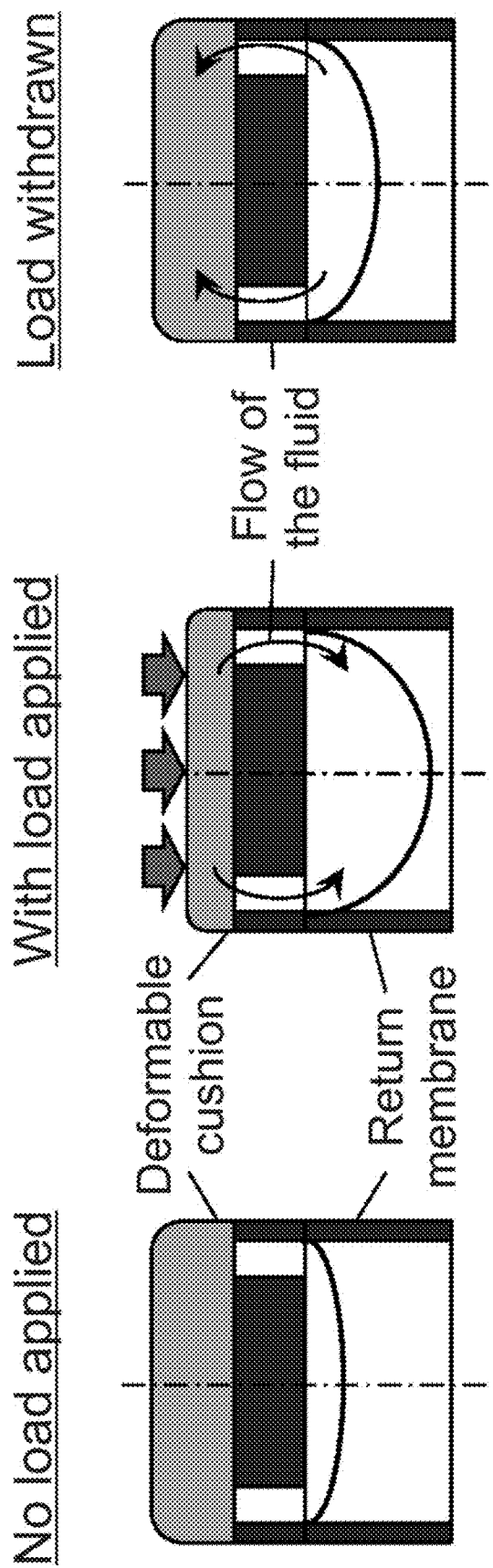
FIGS. 8A to 8C show exemplary views of different states of the variable stiffness module that uses a circular elastic membrane.
Figures 9A, 9B, 9C:
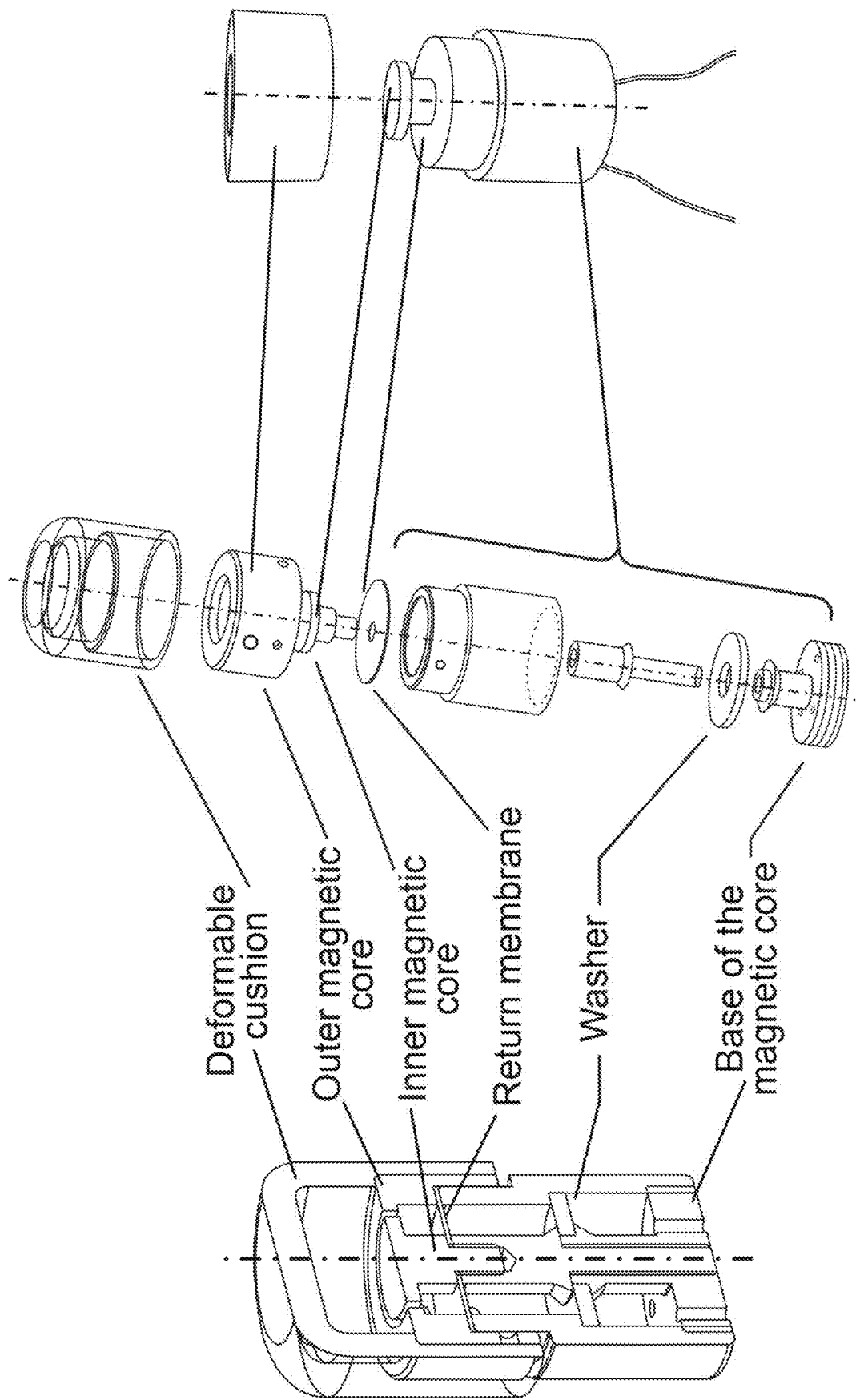
FIG. 9A to 9C show different views of the components that can form the variable stiffness module with the elastic membrane.

In this configuration, the liquid is able to pass from one module/cushion to another through a communication channel. The valve corresponding to each module controls the passage of the fluid from the deformable cushion to the common channel. FIGS. 4 and 5 show a schematic view of the common channel in one embodiment.

This solution ensures greater flexibility, a high level of integration, and simplicity in terms of the design of the overall system.

II. Independent Modules

In this variant, the module constitutes a discrete system. The valve regulates the passage of the liquid between the cushion and the reservoir, thereby controlling the height and the stiffness of the module, as described above.

For correct functioning of the module, it is necessary that the cushion is able to return to its initial (undeformed) configuration/height once the pressure of the foot is withdrawn from said cushion: it is therefore necessary to return the MRF from the reservoir into the cushion. To achieve this function, two different solutions are described below.

1. System with a Plunger Driven by a Spring

When the liquid flows from the cushion into the reservoir on account of the pressure of the foot, the plunger is pushed downward and the spring compresses. Once the pressure of the foot is withdrawn, the spring causes the liquid to rise into the cushion (FIGS. 6A-6C and 7A-7C).

Springs of different stiffness can be used to obtain variable effects.

2. System with a Deformable Elastic Membrane Made of Latex

In this variant, a circular elastic membrane is positioned just below the valve. Once the liquid is pushed downward on account of the deformation of the cushion, the latex membrane (or any other elastic and leaktight element) deforms in order to receive the liquid. It is able to deform until it covers the entire volume of the reservoir. Once the pressure of the foot on the module is withdrawn, the membrane returns to its initial configuration, which causes the liquid to rise toward the cushion (FIGS. 8A-8C and 9A-9C).

It is possible to use membranes of different thickness in order to regulate the restoring force that causes the liquid to rise into the cavity of the cushion.

The invention is not limited to the examples set out in this document. It is possible to use any kind of module that ensures regulation of the pressure acting locally on the skin and subcutaneous tissue.

Moreover, the invention is not limited to a specific geometry, arrangement or size of the modules.

The invention claimed is:

1. A system for locally adjusting a pressure on a skin of a user, the system comprising:
a set of adjacent modules arranged to form a layer, each module of the set of adjacent modules including,
a deformable cushion having a cavity and configured to deform along a longitudinal axis,
a valve,
a housing having a reservoir and a biasing structure, wherein the biasing structure is located in the reservoir, the cavity of the deformable cushion and the reservoir including a liquid fluid, the cavity and the reservoir communicating with the valve, the valve located between the cavity of the deformable cushion and the reservoir, the valve providing for a direct fluidic connection between the cavity of the deformable cushion and the reservoir for liquid fluid exchange, and
a pressure sensor configured to detect a pressure acting directly or indirectly on the deformable cushion, and wherein the deformable cushion comprises a lip that allow sealing of an upper portion of the housing, and
wherein the biasing structure is configured to provide a biasing force that pushes the liquid fluid toward the deformable cushion along the longitudinal axis in response to the deformable cushion pushing the liquid fluid against the biasing structure, and
wherein a position of the valve is configured to be changed to control a flow rate of the liquid fluid between the cavity of the deformable cushion and the reservoir to increase or reduce a deformation of the deformable cushion according to the pressure detected by the pressure sensor.

2. The system as claimed in claim 1, wherein each module of the set of adjacent modules is not in fluidic connection with another module.

3. The system as claimed in claim 1, wherein at least two of the modules of the set of adjacent modules are in fluidic connection with each other.

4. The system as claimed in claim 1, wherein the biasing structure is a spring configured to exert a restoring force in a direction of the deformable cushion.

5. The system as claimed in claim 1, wherein the biasing structure is an elastic membrane configured to exert a restoring force in a direction of the deformable cushion.

6. The system as claimed in claim 1, wherein the liquid fluid comprises a magnetorheological fluid (MRF).

7. The system as claimed in claim 1, wherein the pressure sensor is arranged on an outer face of a wall of the deformable cushion, configured to directly measure an external pressure that acts on the deformable cushion.

8. The system as claimed in claim 1, wherein the pressure sensor is arranged in the cavity of the deformable cushion, configured to measure the pressure inside the cavity.

9. The system as claimed in claim 1, wherein the set of adjacent modules is dimensioned to cover a surface of at least one of a forefoot and a heel.

10. The system as claimed in claim 1, wherein the cavity of the deformable cushion, the valve, and the reservoir of each module form a closed fluidic system.

11. The system as claimed in claim 1, wherein liquid fluid is incompressible.

12. The system as claimed in claim 11, wherein the valve is configured to take an open and a closed position, and in the closed position, the deformable cushion is rigid, while in the open position, the deformable cushion is able to deform by permitting a liquid fluid flow between the cavity of the deformable cushion and the reservoir.

* * * * *